(12) United States Patent
Carrano et al.

(10) Patent No.: US 10,245,585 B2
(45) Date of Patent: Apr. 2, 2019

(54) SPECIMEN DELIVERY APPARATUS

(71) Applicant: Paratus Diagnostics, LLC, San Marcos, TX (US)

(72) Inventors: John C. Carrano, San Marcos, TX (US); Roland Schneider, San Marcos, TX (US); John J. Carrano, San Marcos, TX (US)

(73) Assignee: PARATUS DIAGNOSTICS, LLC, San Marcos, TX (US)

( * ) Notice: Subject to any disclaimer, the term of this patent is extended or adjusted under 35 U.S.C. 154(b) by 0 days.

(21) Appl. No.: 15/620,543

(22) Filed: Jun. 12, 2017

(65) Prior Publication Data
US 2017/0282176 A1 Oct. 5, 2017

Related U.S. Application Data

(63) Continuation of application No. 13/918,877, filed on Jun. 14, 2013, now Pat. No. 9,675,973.

(60) Provisional application No. 61/659,431, filed on Jun. 14, 2012.

(51) Int. Cl.
*B01L 3/00* (2006.01)
*G01N 1/38* (2006.01)

(52) U.S. Cl.
CPC .......... *B01L 3/502* (2013.01); *B01L 2200/06* (2013.01); *B01L 2200/10* (2013.01); *B01L 2200/16* (2013.01); *B01L 2300/041* (2013.01); *B01L 2300/046* (2013.01); *B01L 2300/0636* (2013.01); *B01L 2300/087* (2013.01); *B01L 2300/0867* (2013.01); *B01L 2300/123* (2013.01); *B01L 2400/0481* (2013.01); *B01L 2400/0683* (2013.01); *G01N 1/38* (2013.01)

(58) Field of Classification Search
CPC combination set(s) only.
See application file for complete search history.

(56) References Cited

U.S. PATENT DOCUMENTS

| 6,645,758 | B1* | 11/2003 | Schnipelsky | ........... B01L 3/502 422/547 |
| 2013/0180595 | A1* | 7/2013 | Naunheimer | .......... B01J 8/0492 137/13 |
| 2014/0176939 | A1* | 6/2014 | Shah | .................. G01N 21/8483 356/246 |
| 2015/0307809 | A1* | 10/2015 | Eckelberry | ............. C11B 3/005 435/173.7 |

* cited by examiner

Primary Examiner — Brian R Gordon
(74) Attorney, Agent, or Firm — Cronin PLLC

(57) ABSTRACT

A specimen processing apparatus includes a housing having a fluid supply reservoir, a specimen receiving chamber, a specimen collection reservoir, and an actuator coupled to the fluid supply reservoir. A liquid flow path extends from the fluid supply reservoir to the specimen receiving chamber, and to the specimen collection reservoir. The actuator is operable to propel a liquid from the fluid supply reservoir to the chamber. The specimen receiving chamber includes an inlet port, an outlet port, and a fluid flow guide disposed between the inlet port and the outlet port. In addition, the fluid supply reservoir is fluidly coupled to the inlet port and the outlet port is fluidly coupled to the specimen collection reservoir. The fluid flow guide may be operable to roil a liquid as it flows from the inlet port to the outlet port to facilitate the extraction of a specimen from a collection device.

20 Claims, 17 Drawing Sheets

SPECIMEN DELIVERY APPARATUS

CROSS-REFERENCE TO RELATED APPLICATIONS

This application is a continuation of U.S. patent application Ser. No. 13/918,877 filed on Jun. 14, 2013, now U.S. Pat. No. 9,675,973 entitled SPECIMEN DELIVERY APPARATUS, which claims the benefit of provisional patent application No. 61/659,431, filed Jun. 14, 2012 both of which are incorporated herein by reference.

TECHNICAL FIELD

This invention relates to the field of medical diagnostics. In particular, this invention is drawn to a specimen delivery apparatus for in vitro medical diagnostic devices including point-of-care in vitro medical diagnostic devices.

SUMMARY

In accordance with an illustrative embodiment, a specimen processing apparatus includes a housing having a fluid supply reservoir, a specimen receiving chamber, a specimen collection reservoir, and an actuator coupled to the fluid supply reservoir. A liquid flow path extends from the fluid supply reservoir to the specimen receiving chamber, and to the specimen collection reservoir. The actuator is operable to propel a liquid from the fluid supply reservoir to the chamber. The specimen receiving chamber includes an inlet port, an outlet port, and a fluid flow guide disposed between the inlet port and the outlet port. In addition, the fluid supply reservoir is fluidly coupled to the inlet port and the outlet port is fluidly coupled to the specimen collection reservoir.

In another embodiment, a method of preparing a specimen includes collecting a sample using a collection device. The collection device includes a support substrate and a sample collection material surrounding at least a portion of the support substrate. The method further includes capturing at least a portion of the collection device that includes the sample collection material within a specimen receiving chamber of a specimen processing apparatus. The specimen receiving chamber includes an inlet port, and an exit port.

Other features and advantages of the present invention will be apparent from the accompanying drawings and from the detailed description that follows below.

BRIEF DESCRIPTION OF THE DRAWINGS

The present invention is illustrated by way of example and not limitation in the figures of the accompanying drawings, in which like references indicate similar elements and in which.

DETAILED DESCRIPTION

Approaches to diagnosing medical ailments often entail collecting a sample from a patient, preparing a specimen from the sample, analyzing the specimen to assay the presence of various biological or chemical analytes (i.e., substances whose chemical constituents are being identified), and interpreting the presence and amount of the analytes or their absence to derive a diagnosis. The study of samples of tissues and bodily fluids outside of the body is referred to as in vitro analysis.

Figure 1:
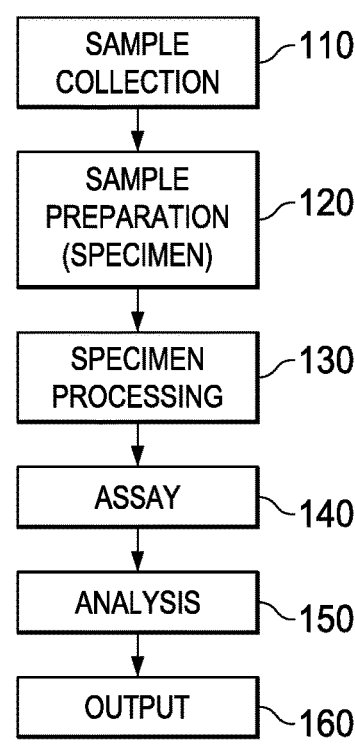
FIG. 1 illustrates an embodiment of a functional block diagram for performing a medical diagnosis.

FIG. 1 illustrates one embodiment of a process for performing an in vitro medical diagnosis. A sample of the tissue, fluid, or other bodily matter is collected in step 110. The sample is typically prepared in order to form a specimen in step 120. Preparation of the sample might include, for example, elution, mixing, or lysing in order to produce a specimen. The specimen may therefore be considered to be a portion of, or product of, the sample that may be assayed to determine whether a target analyte is or was present in the sample. In some cases, the sample serves as a specimen as collected. Further specimen processing may be performed at step 130.

After specimen processing, an assay is performed in step 140. In vitro analysis examines specimens for biological or chemical components. The assay may be qualitative, quantitative, or both. An analysis of the assay results is performed in step 150. The result of the analysis is then output in step 160.

The sample may be collected from a patient at the point of care. The remaining steps may be performed on- or off-site or in any combination thereof. For example, samples or specimens may be sent to offsite laboratories with sophisticated equipment and highly trained laboratory personnel that process the specimen for analysis. To the extent these functions can be incorporated into a point-of-care medical diagnostic system, the cost and length of time required for diagnosing an ailment may be reduced considerably. The lead time for treatment as well as the cost for treatment may likewise be reduced. The medical diagnostic device may also indirectly protect populations other than the patient, particularly when dealing with detecting contagious diseases and assessing aggregate data for timely determining the onset or scope of an epidemic. Point-of-care medical diagnostic devices can offer significant healthcare benefits.

With respect to incorporating the process of FIG. 1 into a point-of-care medical diagnostic system, the functional blocks may be distributed across a number of components in order to enable economically efficient and practice efficient in vitro medical diagnostic devices.

Figure 2A:
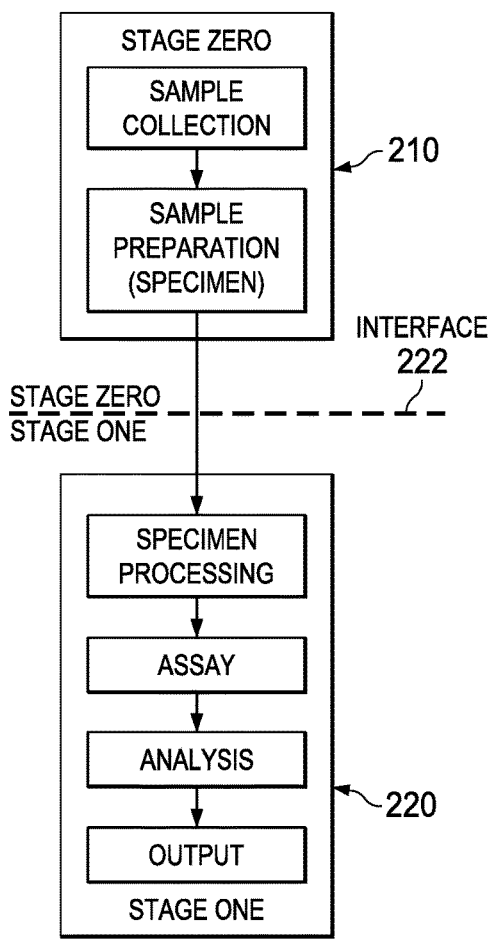
FIGS. 2A and 2B illustrate embodiments of a modular staged point-of-care medical diagnostic system.
Figure 2B:
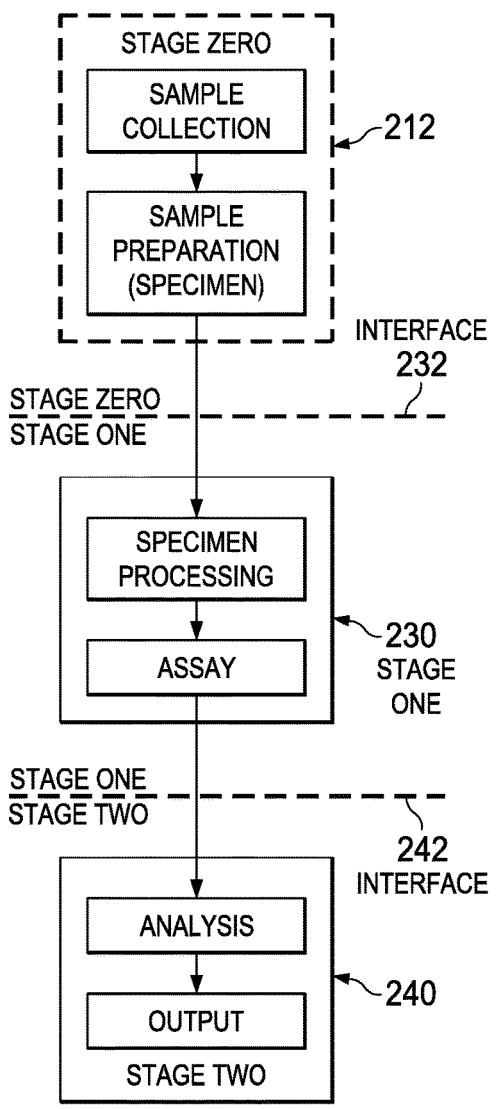

Referring to FIGS. 2A and 2B, for example, in one embodiment of an in vitro medical diagnostic system, the functional blocks including sample acquisition and sample preparation are incorporated into stage zero component 210. Functional blocks including specimen processing, assay, analysis, and output are incorporated into one or more components.

In one embodiment, functional blocks including specimen processing and assay are incorporated into a stage one component 230. Functional blocks for analysis and output are incorporated into another component, stage two component 240. In an alternative embodiment, specimen processing, assay, analysis, and output are incorporated into a single component, the stage one component 220.

The distribution among various components enables staging of the medical diagnostic system to facilitate both practice and economic efficiency, as any component directly handling specimens will either have to be disposed of or alternatively sterilized before re-use.

In one embodiment, stages zero and one are disposable components. The analysis function is generally a computational function. If cost efficient or practice efficient to do so, the analysis function may be incorporated into a disposable component. In one embodiment, however, the analysis function is incorporated into a subsequent stage ("stage one" or "stage two") component that need not be disposed of Modular staging enables the greatest flexibility to allocate diagnostic functions between components to realize practice and cost efficiencies.

The stages interface with a person or each other at various interfaces. In a point-of-care medical diagnostic system, physical coupling between stage one and any subsequent stage likely only needs to support electrical or optical signals. The electrical and signaling interface between stage one and any subsequent stage may be proprietary. Training requirements for coupling such stages together is minimal. Thus, for example, the stage one/stage two interface 242 might consist simply of an electrical connector.

The stage zero/stage one interface 222, 232 is likewise designed for ministerial level skills. Although different versions of specimen delivery systems (stage zero) might be necessary to accommodate different types of samples or different specimen preparation processes, for example, the use of a standardized interface such as a snap-in or plug-in type of coupling ensures that only ministerial skill levels are needed to couple the specimen delivery apparatus to the next modular stage of the point-of-care medical diagnostic system.

In contrast, the interface between the patient and stage one may be indirect and involve a number of steps that previously required significant skills or training and equipment. Acquisition of typical samples from a patient is largely a mechanical task and does not require significant training. Typical samples, for example, consist of fluids or tissue. Collection of these samples is performed by a clinician or provided by the patient using standard clinical techniques (e.g., blood, dried blood, urine, sputum, mucous, etc.). In many instances, the sample is obtained by swabbing a patient's body or the inside of a container that contains sample material.

Sample preparation can impose much greater training requirements. Sample preparation might be performed by a laboratorian and is susceptible to variations in user experience, skill set, and preparation environmental conditions. In addition, sample preparation often requires additional equipment for measuring and mixing along with a separate inventory of the items that the sample would be mixed with. In this disclosure, a specimen delivery apparatus, which may also be referred to as a specimen processing apparatus, is proposed that reduces or eliminates the need for skilled practitioners or laboratory personnel to perform many of such sample preparation processes in order to produce or deliver a specimen.

Traditional clinical practices for obtaining samples from the patient may be utilized to collect the sample, and although the functions performed by the specimen delivery apparatus might qualify as complex, those functions may be largely abstracted from the user. In particular, the user performs low-complexity tasks (e.g., select an appropriate specimen delivery apparatus, place the sample in the specimen delivery apparatus, close the selected specimen delivery apparatus, attach the specimen delivery apparatus to a subsequent stage apparatus or system, and actuate the specimen delivery apparatus). The specimen delivery apparatus may be configured to support various samples and sample preparation needs.

Figure 3A:
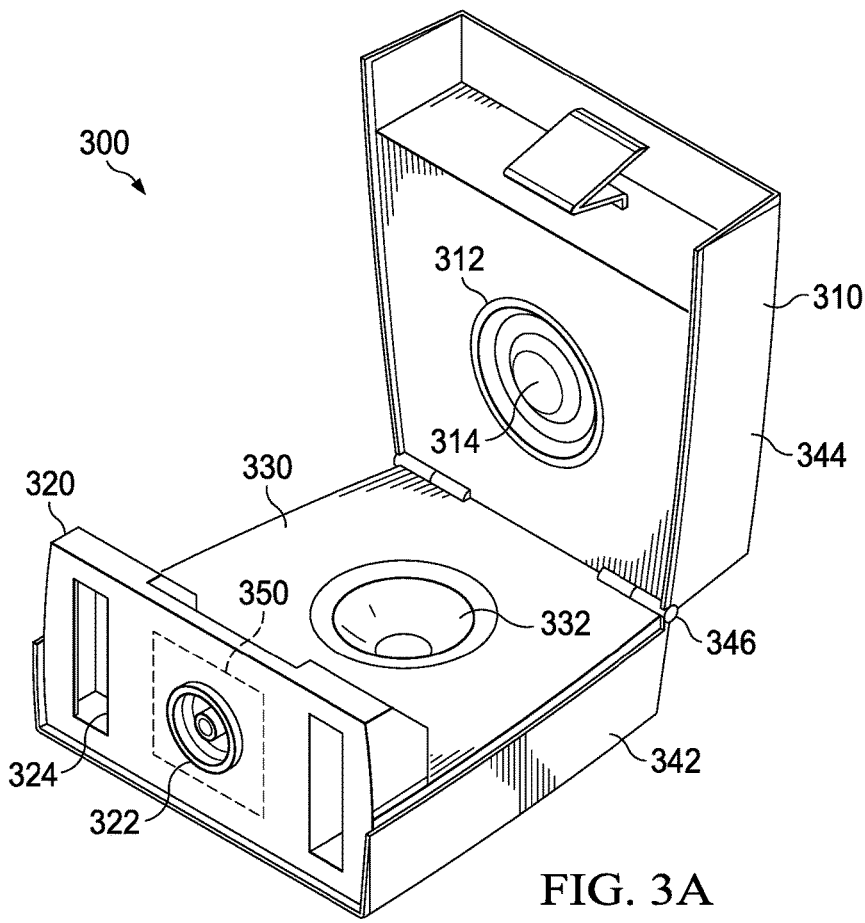
FIGS. 3A-3C illustrate embodiments of a specimen delivery apparatus.
Figure 3B:
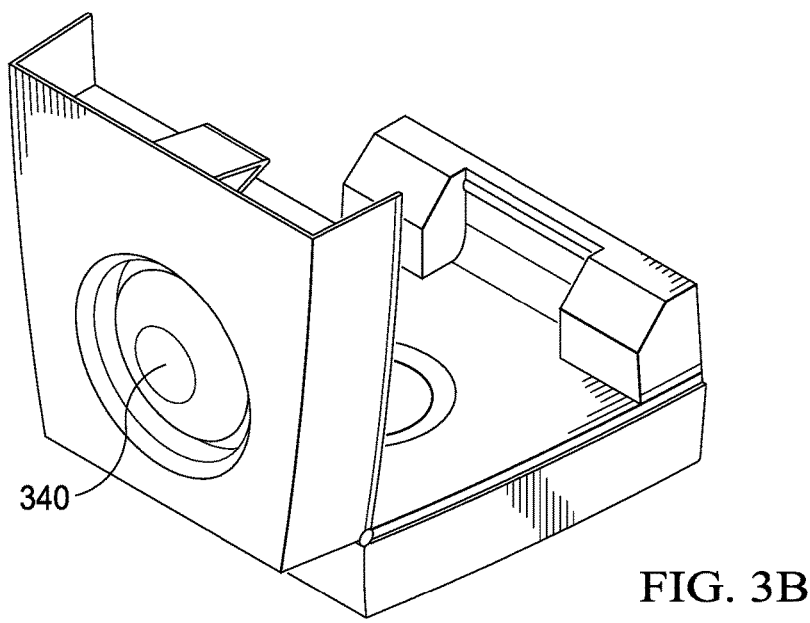
Figure 3C:
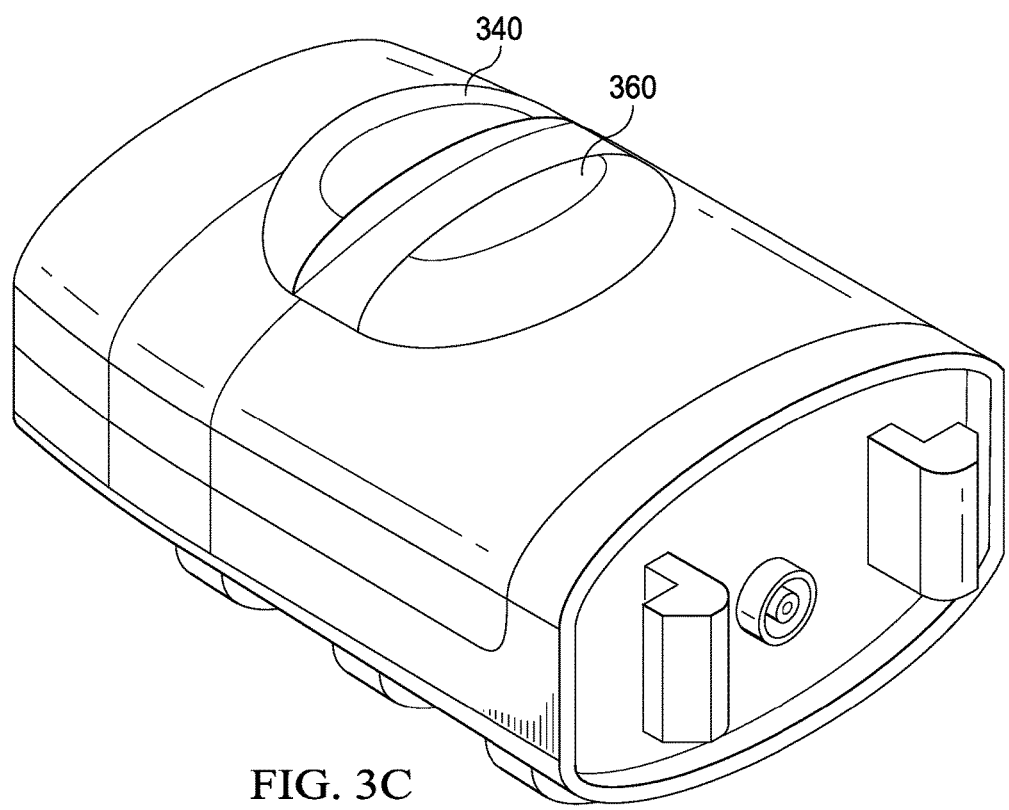

FIGS. 3A-3C illustrate an embodiment of a specimen delivery apparatus 300. The specimen delivery apparatus 300 includes a housing 310 having a first portion 342 and a second portion 344 coupled at a hinge 346. The housing 310 has an open state and a closed state. In one embodiment, the housing 310 is hinged such that the housing 310 may be closed by moving the second portion 344 toward the first portion 342. The housing 310 includes a backplane 320 that includes at least one fluid communication port 322, and may thereby be referenced as an interfacing surface. A midplane 330 serves as an intermediate portion having a cavity 332 for holding a sample. The midplane 330 is sealed within and positioned between the first portion 342 and second portion 344 of the housing 310 when the housing 310 is in the closed state.

In one embodiment, the housing 310 includes locking features to secure the housing 310 in a closed state once closed. Thus a sample may be placed in the housing 310 in the open state. Once closed, the features prevent the housing 310 from being opened back up. Such features aid in the containment of medical waste.

A first actuator 340 is disposed to move fluid within the housing when the housing is in the closed state and the first actuator is actuated. In the illustrated embodiment, the first actuator is a bulb and is referred to as first bulb 340. A destructible seal 350 prevents fluid communication through the fluid communication port while the seal is intact. Actuation of the first bulb 340 communicates fluid through the fluid communication port when the destructible seal is not intact.

In one embodiment, the specimen delivery system includes a second actuator or second bulb 360. Alternate actuation of the first and second bulbs moves fluid within the housing when the destructible seal is intact. Actuation of the first or second bulb moves fluid through the fluid communication port when the destructible seal is not intact.

In one embodiment, a "locking" mechanism is employed for one or more bulbs. The locking mechanism maintains the bulb in a depressed position once actuated. One embodiment of the locking mechanism includes a shell covering a flexible portion of the bulb. The shell includes features to latch onto mating features of the housing when depressed. The locking mechanism prevents the specimen delivery apparatus from drawing or siphoning fluid back through the fluid communication port. The locking mechanism also serves to provide visual feedback indicative of a used specimen delivery apparatus. Another advantage of a bulb locking mechanism includes tactile feedback for the user: when the locking mechanism "snaps" into place and retains the bulb, the user may be confident that the user has completed the delivery task.

In one embodiment, the backplane includes at least one attachment point 324 for mechanically coupling the specimen delivery apparatus to a subsequent stage of the point-of-care medical diagnostic system. When coupled via the attachment point, the fluid communication port of the specimen delivery apparatus is aligned with a fluid communication port of the subsequent stage to enable fluid communication between the specimen delivery apparatus and the subsequent stage. In one embodiment, the attachment point includes features to prevent de-coupling of the specimen delivery apparatus and subsequent stage once coupled.

To facilitate sample preparation, the housing 310 includes a blister pack retainer 312. A blister pack 314, which acts as a fluid supply reservoir containing a sample preparation fluid is placed in the blister pack retainer 312. In one embodiment, closing the housing 310 causes the blister pack 314 to burst and release its contents. In an alternative embodiment, the first bulb 340 is disposed such that actuation of the first bulb when the housing is closed causes the blister pack 314 to burst and release its contents.

The use of a blister pack 314 substantially eliminates the need to have external laboratory equipment, supplies, or skilled personnel for sample preparation. The blister pack 314 may be selected for the appropriate sample preparation.

In one embodiment, the blister pack contains a fluid for mixing with and carrying the sample in suspended, diluted, or dissolved form. In another embodiment, the blister pack contains a reagent such as a lysing agent to react with the sample. In one embodiment, the blister pack contains an elution buffer. In another embodiment, the blister pack contains an anti-coagulant. In yet another embodiment, the blister pack contains a solvent to enable extraction of the sample from any carrier it has adhered to. For example, a solvent may be appropriate to extract mucous or similar such samples from a swab.

In one embodiment, a fluid transport tube is coupled to carry fluid from the cavity to the fluid communication port. In one embodiment, the fluid transport tube is rifled to enhance mixing of fluids transported from the cavity to the fluid communication port.

Figure 4B:
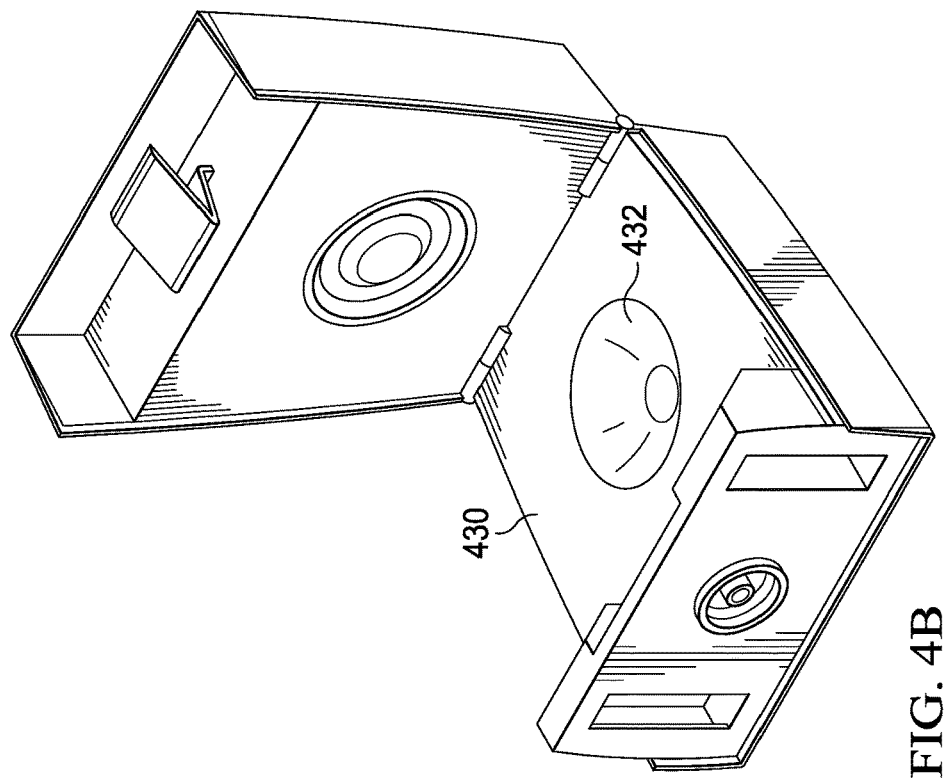
FIGS. 4A-4C illustrate variations on the form factor of the cavity of the specimen delivery apparatus midplane.
Figure 4A:
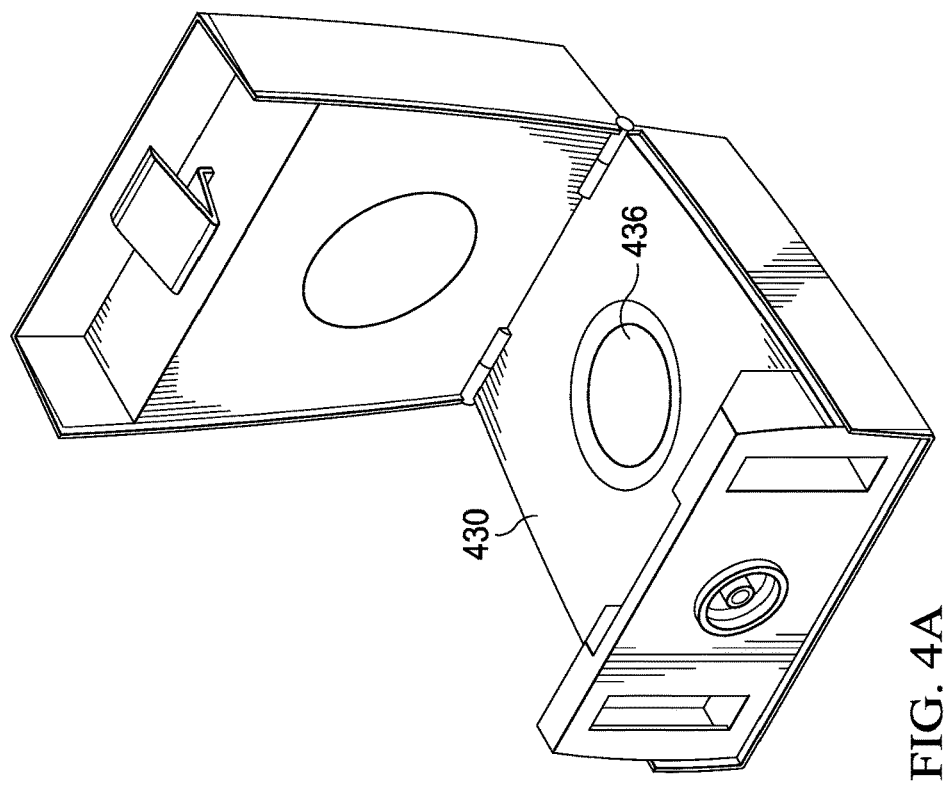
Figure 4C:
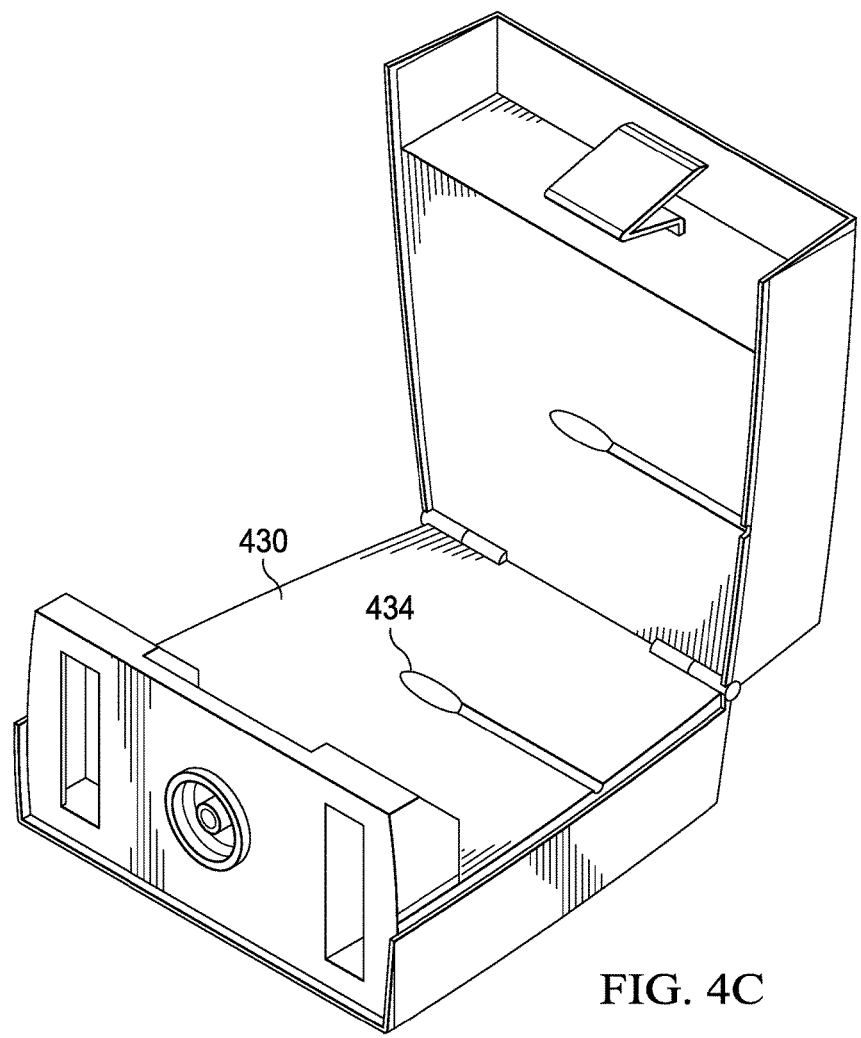

FIGS. 4A-4C illustrate variations on the form factor of the cavity of the midplane 430. The form factor is chosen to facilitate a particular clinical technique or volume associated with the sample being collected. Frequent sample types or sources include blood, urine, tissue, sputum, and mucous.

For example, a hemispheroidal cavity 432 may be appropriate for liquids such as urine or blood. A cavity having a longitudinal cross-sectional profile substantially the same as that of a swab 434 or other suitable sample collection device is used for samples collected by and carried by swab. In one embodiment, the midplane has an open cavity 436 having a cylindrical portion. Here, it is noted that the specimen delivery apparatus described herein may be suitable for use with any suitable type of sample collection device, and that the swab 434 is generally shown and described as a representative sample collection device. Suitable examples of a sample collection device include a cotton swab, a flocked swab, a brush, a sponge, an absorbent surface comprised of several possible materials (e.g. paper, polymer, etc.), or any other implement that can collect particulates, pathogens and fragments of a particular specimen type (including, but not limited to nasal pharyngeal, stool, blood, urine, vaginal, urethral, etc . . . ).

Figure 5:
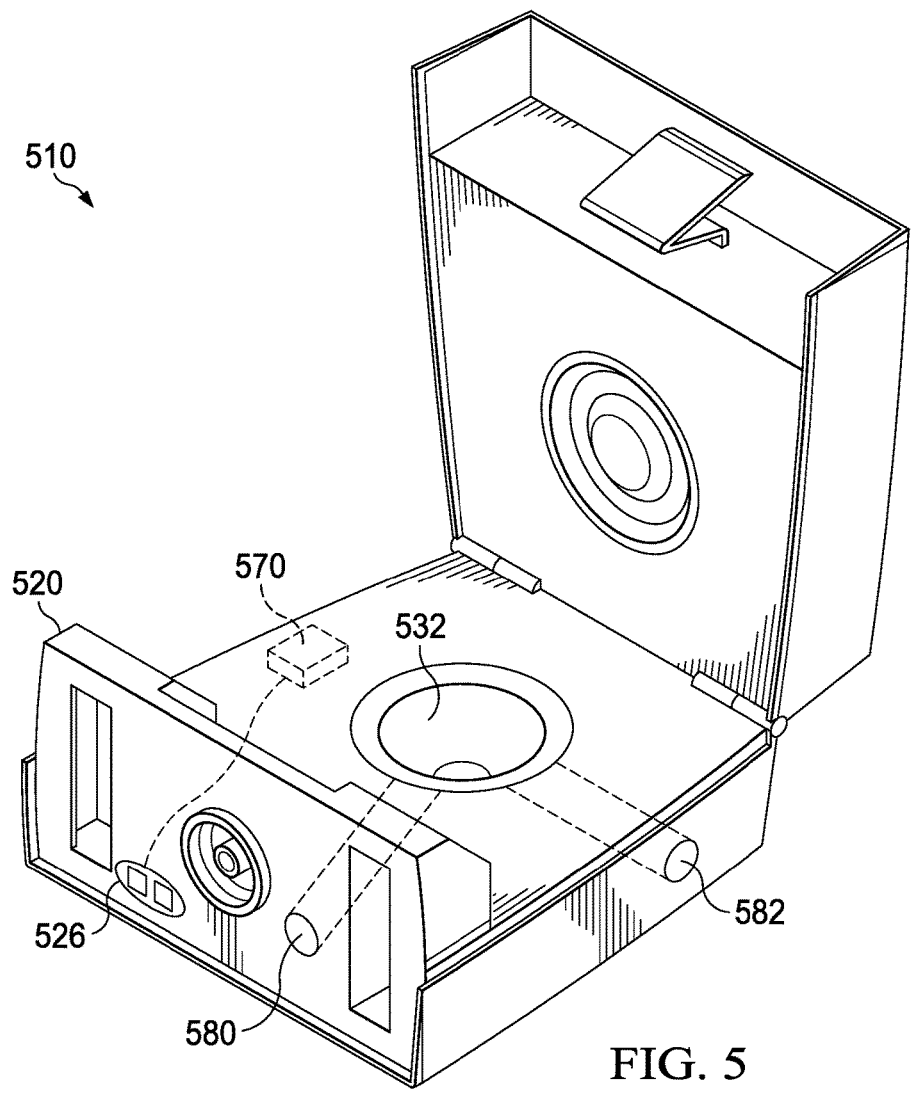
FIG. 5 illustrates another embodiment of the specimen delivery apparatus.

FIG. 5 illustrates another embodiment of the specimen delivery apparatus 510. Backplane 520 includes an electrical port 526 for communication of electrical power to an element 570 within the apparatus. In one embodiment, element 570 is a transducer coupled to the electrical port for applying at least one of a thermal, mechanical, acoustical, or optical energy to the fluid upon application of electrical power to the electrical port.

In one embodiment, the electrical port enables communication of electrical power directly to fluid within the cavity 532 of the apparatus upon application of electrical power to the electrical port. Such a feature may be used to enable lysis via pulsed application of power.

In one embodiment, element 570 is a heater for heating fluid within the apparatus upon application of power to the electrical port. Thermal energy may be used for lysis or sanitization. In one embodiment, element 570 is an acoustic transducer for application of acoustic energy to fluid within the apparatus. Acoustic energy may be used to create cavitation and heat within the fluid sufficient to cause lysis within various biological substances. In one embodiment, the acoustic transducer is a piezoelectric element.

The apparatus may include one or more optical ports 580, 582. In one embodiment, an optical port is included to enable inspection of the contents of the specimen delivery apparatus. In one embodiment, an optical port is included to enable the application of optical energy to the contents of the specimen delivery apparatus.

Figure 6:
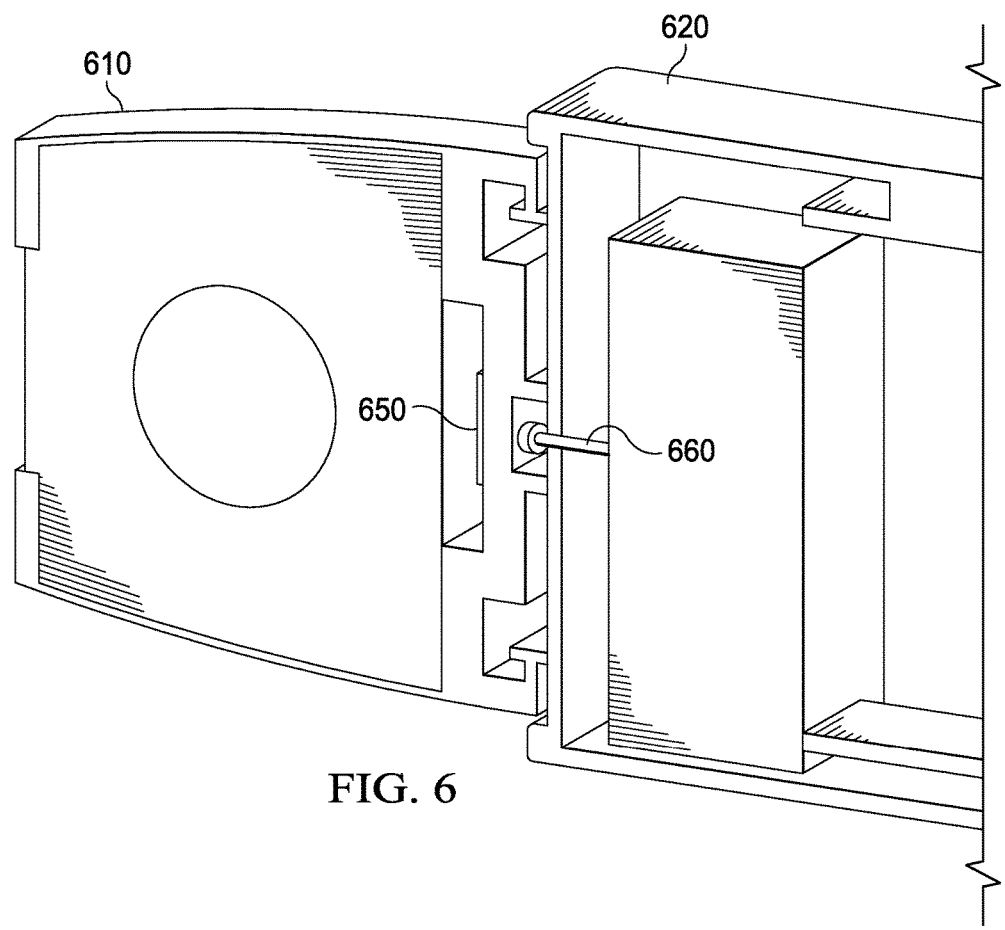
FIG. 6 illustrates attachment of the specimen delivery apparatus to another device.

FIG. 6 illustrates the attachment of the specimen delivery apparatus 610 to the next stage 620 of the point-of-care medical diagnostic system. Upon attachment, the destructible seal 650 is pierced (e.g., by piercing probe 660) such that it is no longer intact. Actuation of a bulb of the specimen delivery apparatus forces fluid communication of the specimen from the specimen delivery apparatus to the next stage of the point-of-care medical diagnostic system.

Figure 7A:
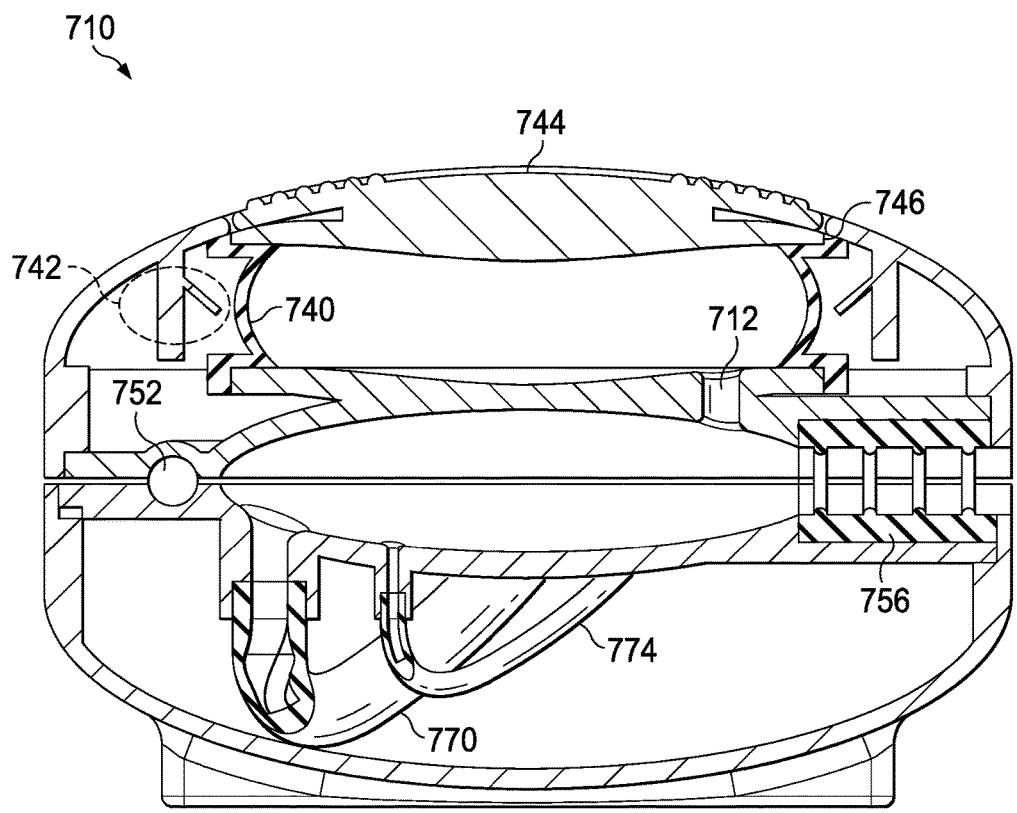
FIGS. 7A and 7B illustrate a cross-section of an embodiment of a specimen delivery apparatus with a bulb locking mechanism.
Figure 7B:
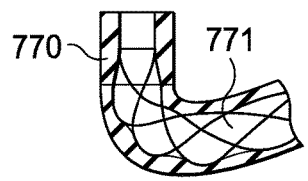

FIGS. 7A and 7B illustrate a cross-section of one embodiment of the specimen delivery apparatus 710 with a bulb locking mechanism. The housing includes retaining apparatus 742 to maintain the bulb 740 in a depressed position once actuated. A shell 744 covers the flexible portion of the bulb.

The shell includes latching features 746 to latch onto or to be retained by the retaining apparatus. The locking mechanism prevents the specimen delivery apparatus from drawing or siphoning fluid back through the fluid communication port. Once the shell is depressed sufficiently to capture or to be captured by the retaining apparatus, the bulb will be maintained in a depressed position. The bulb locking mechanism provides tactile feedback for the user: when the locking mechanism "snaps" into place and retains the bulb, the user may be confident that the user has completed the delivery task. In addition, the locking mechanism provides visual feedback indicative of a used specimen delivery apparatus.

FIG. 7A also illustrates a midplane configured for a swab or other suitable sample collection device. One or more seals 752 serve to prevent the sample from escaping the sampling apparatus through unintended routes. In one embodiment, the midplane and housing include features that co-operate to form at least one swab shaft seal 756. The swab shaft seal(s) assist in preventing the sample from escaping along the shaft of the swab or other suitable sample collection device.

In one embodiment, rather than using a separate blister pack the bulb 740 may be filled with the fluid to be mixed with the sample. In the illustrated embodiment, the fluid is propelled through tube 712 into the sample chamber that is adapted for a swab or other suitable sample collection device.

The fluid transport path transports the fluid to a location internal or external to the specimen delivery apparatus. The fluid transport path may include a portion of the midplane as well as channels, tubes, or intermediate storage mechanisms. The fluid transport path itself may include features to facilitate extracting the sample and mixing the sample with the fluid to prepare and transport the specimen.

For example, the fluid transport path may include channels or fluid transport tube(s) 770, 774 to transport the fluid to a location internal or external to the specimen delivery apparatus. The channel or fluid transport tube(s) may be rifled or have rifling 771 as indicated by the callout for fluid transport tube 770 in order to enhance mixing and transport of the fluid and sample. Here, "rifling" refers to spiral or spiral-like ridges or grooves on the inner surface of the fluid transport tube 770. Features such as the rifling cause the fluid and material carried by the fluid to roil. The roiling effect aids in mixing and transport.

As referenced herein, "roiling" refers to the manipulation of a fluid in a manner that induces mixing and, in particular, extraction of a specimen for analysis from a swab or other sample collection device. For example, testing of the features described in the present disclosure, including the features of the chamber 1610 referenced above (e.g., helical or spiral features that induce vortex flow or spiral-like flow patterns, such as groove 1616) show that the devices disclosed herein induce high fluid shear forces, increase turbulent energy and result in a higher Reynolds number. The foregoing characteristics may be understood to enhance the ability to extract a specimen for analysis from a swab or other sample collection device placed in the chamber 1610. For clarity, it is noted that in the context the sample preparation described in this disclosure, "extraction" does not relate to pulling DNA from a cell. Instead, "extraction" refers generally to the ability to recover organisms, molecules or other particles of interest off from a collection device and deliver those particles to a subsequent stage for further analysis.

In one embodiment, the specimen delivery apparatus includes a validation cache. The purpose of the cache is to retain a clinically relevant amount of the sample within the housing in order to permit independent testing. Fluid transport tube 770 carries the fluid to a fluid communication port. Fluid transport tube 774 carries fluid to the cache.

Figure 8A:
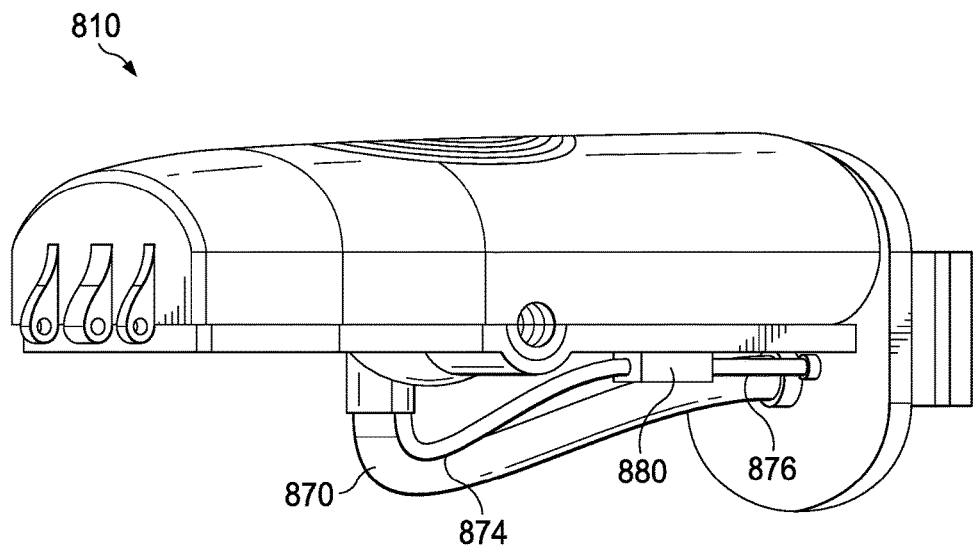
FIGS. 8A-8B illustrate an embodiment of the specimen delivery apparatus with a validation cache.
Figure 8B:
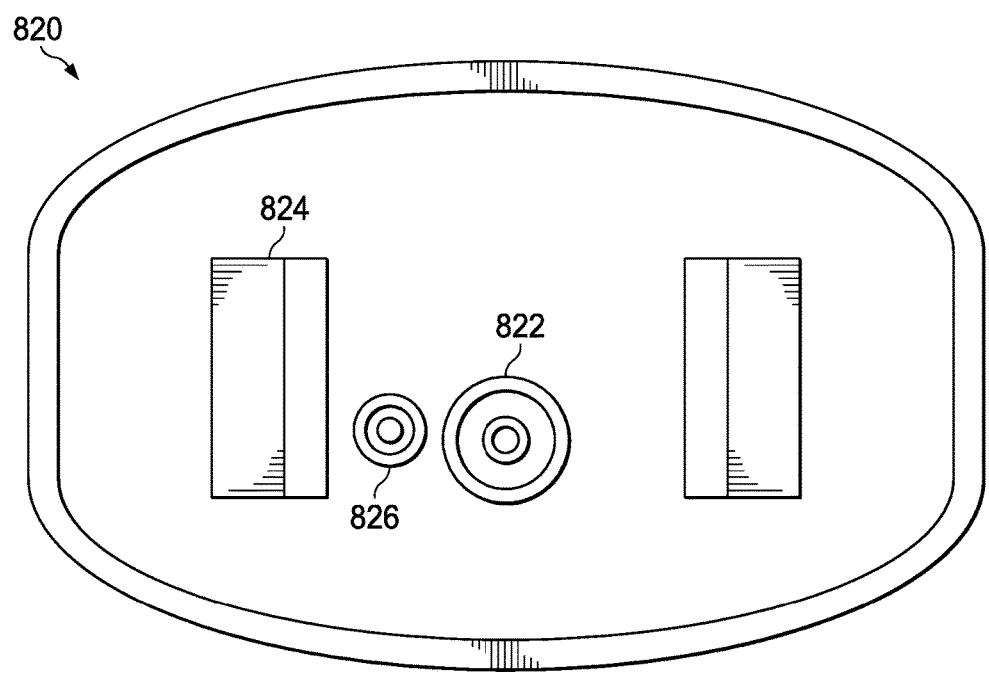

FIG. 8A illustrates a side view of a cutaway of one embodiment of the specimen delivery apparatus 810 including a validation cache 880, and FIG. 8B illustrates a front view of the backplane 820. FIG. 8A shows that a fluid transport tube 874 is provided to carry fluid to the cache. In one embodiment another fluid transport tube 876 carries fluid away from the cache. In alternative embodiments, the contents of the cache may be accessed by extraction through other apparatus such as a stopper as found with vials and ampules.

As shown in FIG. 8B, a front view of the backplane 820 illustrates the primary fluid communication port 822 to be used with next stage point of care. Generally although a fluid transport tube 876 might couple the cache to a cache fluid communication port 826, the next stage device utilizing the primary fluid communication port 822 will not be the same device that utilizes the cache fluid communication port 826. In the field, the attachment points 824 coupling the specimen delivery apparatus to the next stage prevent field separation of the specimen delivery apparatus and the next stage. In one embodiment, a special tool may be utilized to permit separation of the specimen delivery apparatus and the next stage in order for the validation lab to gain access to a cache fluid communication port 826 positioned on the backplane 820.

Figure 9:
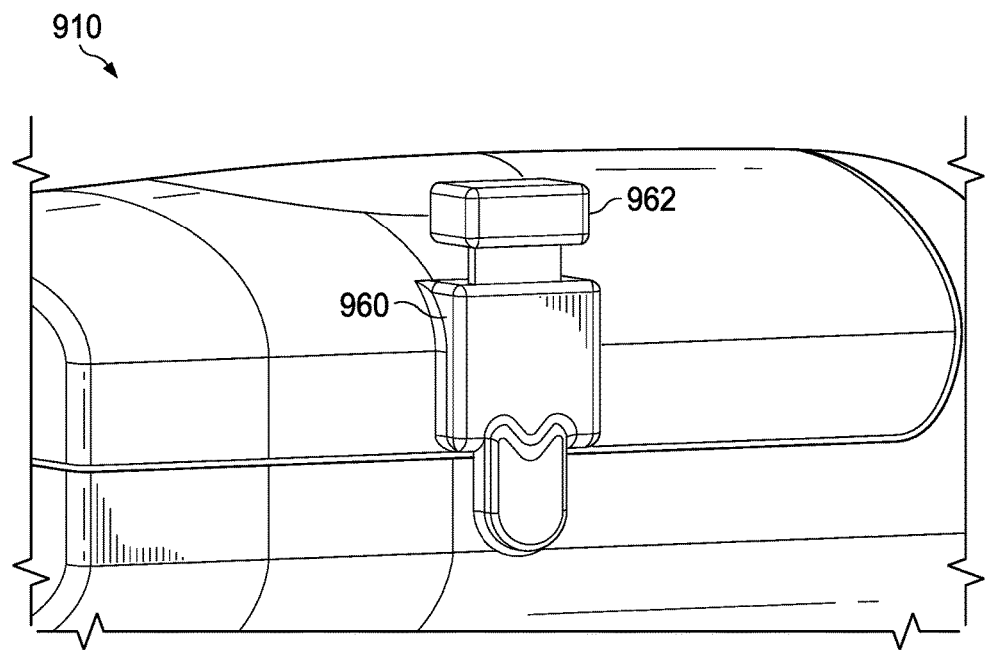
FIG. 9 illustrates an embodiment of a swab cutter for a specimen delivery apparatus.

The shaft portion of a swab or other suitable sample collection device is a nuisance once the sample is acquired and placed within the specimen delivery apparatus. A swab may have a pre-scored shaft to facilitate breaking off the shaft after the sample is disposed within the specimen delivery apparatus. Alternatively the specimen delivery apparatus may include a swab cutter to neatly trim away excess swab shaft material. FIG. 9 illustrates one embodiment of a swab cutter 960 for a specimen delivery apparatus 910. The swab cutter includes a blade (not shown) or other cutting apparatus coupled to the button 962. After placement of the swab or other suitable sample collection device in the specimen delivery apparatus and closing specimen delivery apparatus, the button 962 of the swab cutter may be depressed to sever the shaft of the swab or other suitable sample collection device.

The fluid transport path may be configured to accomplish goals in addition to transport. As addressed above, channels or fluid transport tubes can include rifling or other features to facilitate transport and mixing. In some cases, the sample may be carried by a tool such as a swab from which the sample must be stripped in order to prepare the specimen. When the specimen delivery apparatus is in the closed position, the swab or other suitable sample collection device is held within a chamber formed by the housing and the midplane cavity. In order to extract more sample from the swab or other suitable sample collection device, the chamber may include features to create a roiling effect when fluid is driven into the chamber. The chamber forms a portion of the fluid transport path. Thus the fluid transport path may include features to strip or extract, mix, and carry the sample when preparing the specimen.

Figure 10:
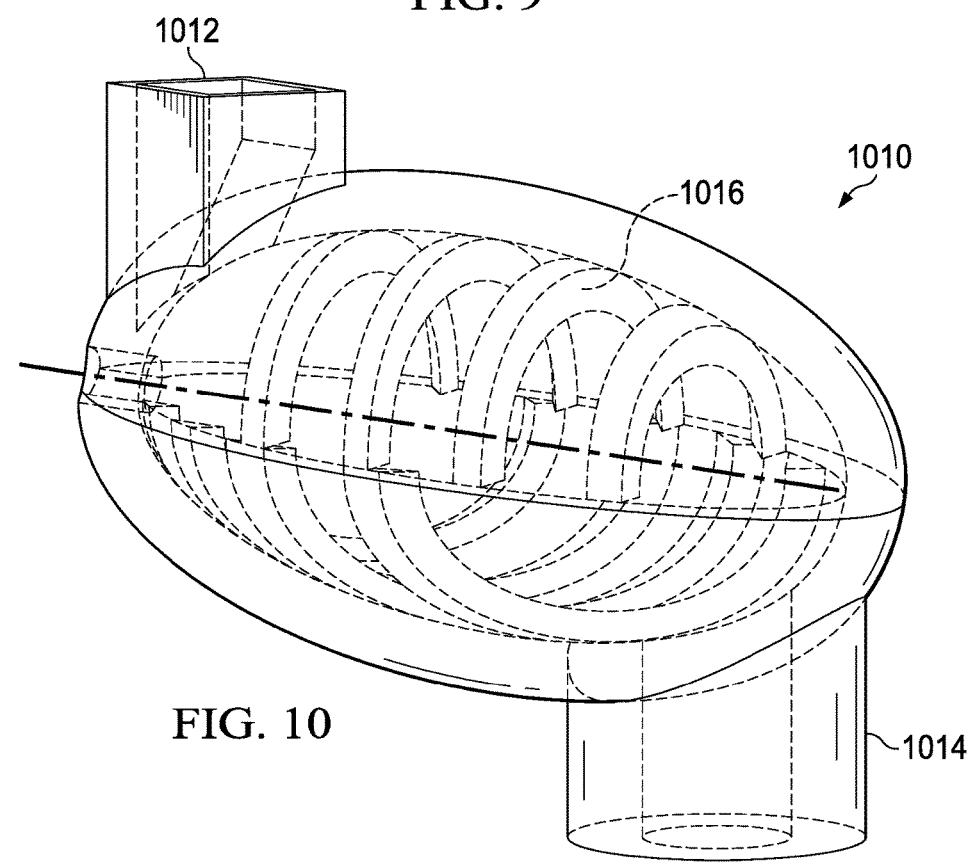
FIG. 10 illustrates an embodiment of a chamber containing a swab when the specimen delivery apparatus housing is in the closed position.

FIG. 10 illustrates the chamber 1010 containing the swab or other suitable sample collection device when the specimen delivery apparatus housing is in the closed position. The chamber includes an inlet port 1012 that receives fluid from the bulb or blister pack and directs fluid flow into the chamber 1010 along the circumference of the wall of the chamber to induce a vortex effect of circular or spiral flow as the fluid flows about the chamber 1010 from the inlet port 1012 to an exit port 1014. The exit port 1014 provides for the fluid and sample to be carried to the remainder of the fluid transport path. The chamber 1010 has roiling features 1016, which may be grooves, raised thresholds, or other features to direct the fluid. In the illustrated embodiment, the features 1016 are raised portions, forming grooves between the raised portions in a helical or spiral structure.

Figure 11:
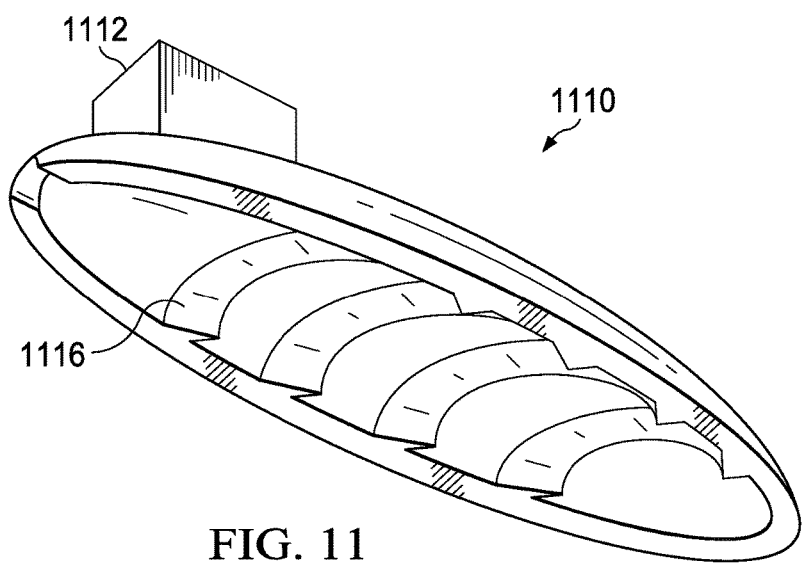
FIG. 11 illustrates an embodiment of the upper portion of the chamber of FIG. 10 with roiling features.
Figure 12:
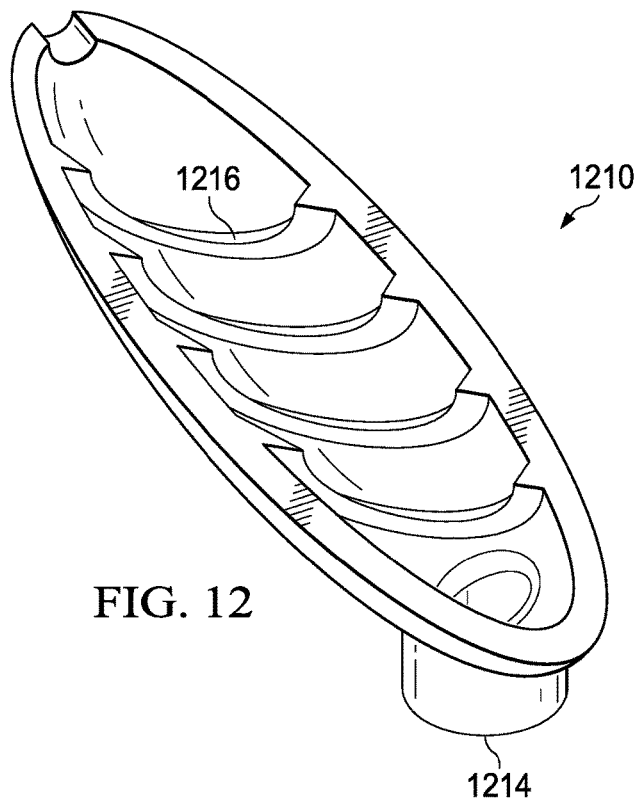
FIG. 12 illustrates an embodiment of the lower portion of the chamber of FIG. 10 with roiling features.

FIG. 11 illustrates one embodiment of the upper portion 1110 of the chamber including the inlet port 1112 and the grooved or raised features (e.g. a baffle or fluid flow guide) 1116 that form a portion of the fluid transport path. FIG. 12 illustrates one embodiment of the lower portion 1210 of the chamber including the exit port 1214 and the grooved or raised features 1216 that form a portion of the fluid transport path. In an embodiment, one or more of the raised features 1216 comprises a chamfered edge, as shown in FIG. 12. The grooved or raised features of the chamber increase the shear forces of the fluid and direct the fluid across the surface of the swab or other suitable sample collection device to extract the sample from the swab or other suitable sample collection device. The roiling effect caused by these features also enhances mixing of the fluid with the sample.

Figure 13:
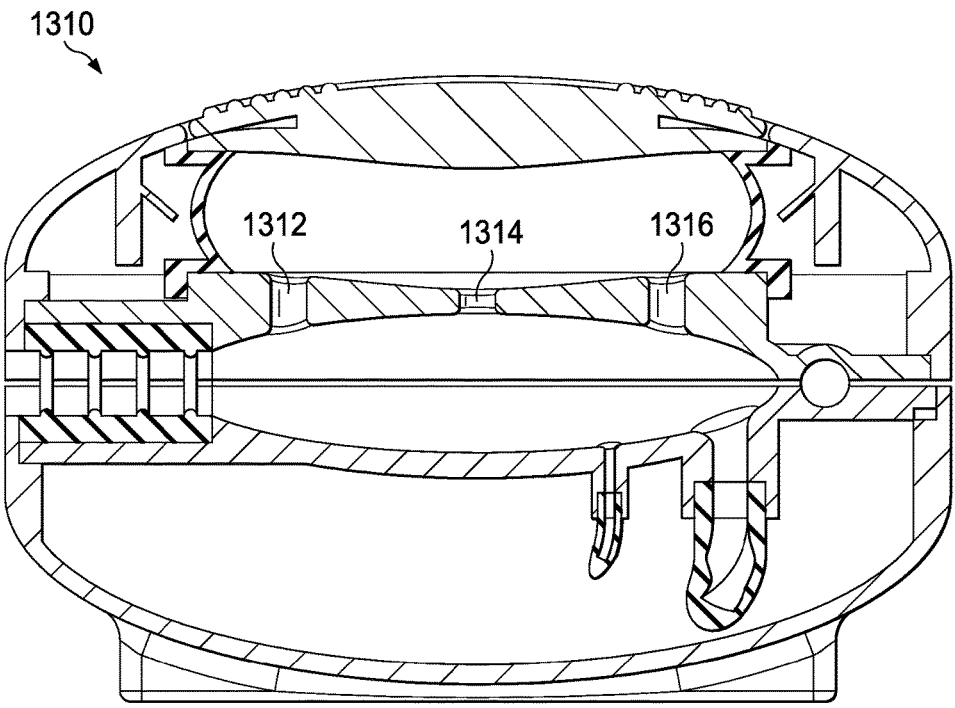
FIG. 13 illustrates an embodiment of a specimen delivery apparatus having multiple entry points for communicating fluid into the chamber.

The housing and midplane may be configured to provide for multiple entry points of fluid into the fluid transport path. FIG. 13 illustrates one embodiment of a specimen delivery apparatus 1310 having multiple entry points 1312, 1314, 1316 for communicating fluid from the bulb or blister pack into the sample chamber.

In one embodiment, the specimen delivery apparatus includes a staging chamber to separate the function of specimen preparation and specimen delivery to the next stage. For example, reagents in the transport fluid may require time beyond the transport time to fully act upon the sample. Electrical, thermal, or acoustic lysis may require time beyond the fluid transport time to complete.

Figure 14:
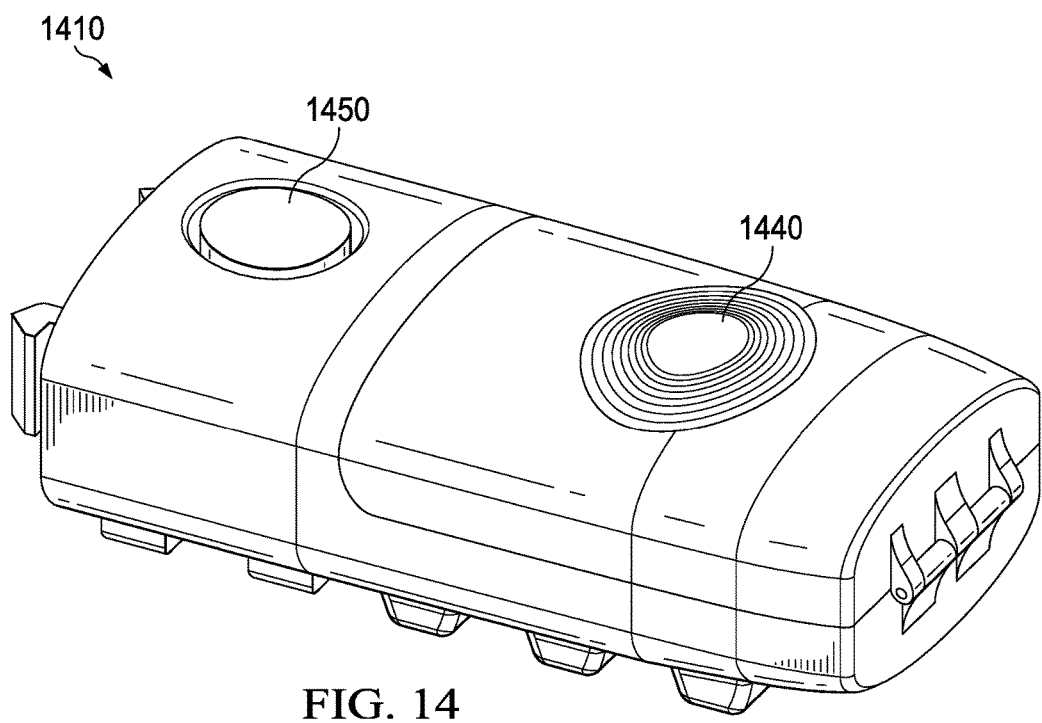
FIG. 14 illustrates an embodiment of a staging or "dual action" specimen delivery apparatus.

FIG. 14 illustrates one embodiment of a staging or "dual action" specimen delivery apparatus 1410. Depressing the first actuator 1440 performs some mixing of the sample with a fluid and transports the fluid with sample to a staging chamber (not shown). A second actuator 1450 propels the prepared specimen to the next stage. The first actuator may be a "bulb" as previously described in one embodiment. The second actuator may be a bulb or any other apparatus for driving the specimen from the chamber to the next stage through the fluid communication port of the specimen delivery apparatus. The first and second actuators are fluid transport actuators.

Figure 15:
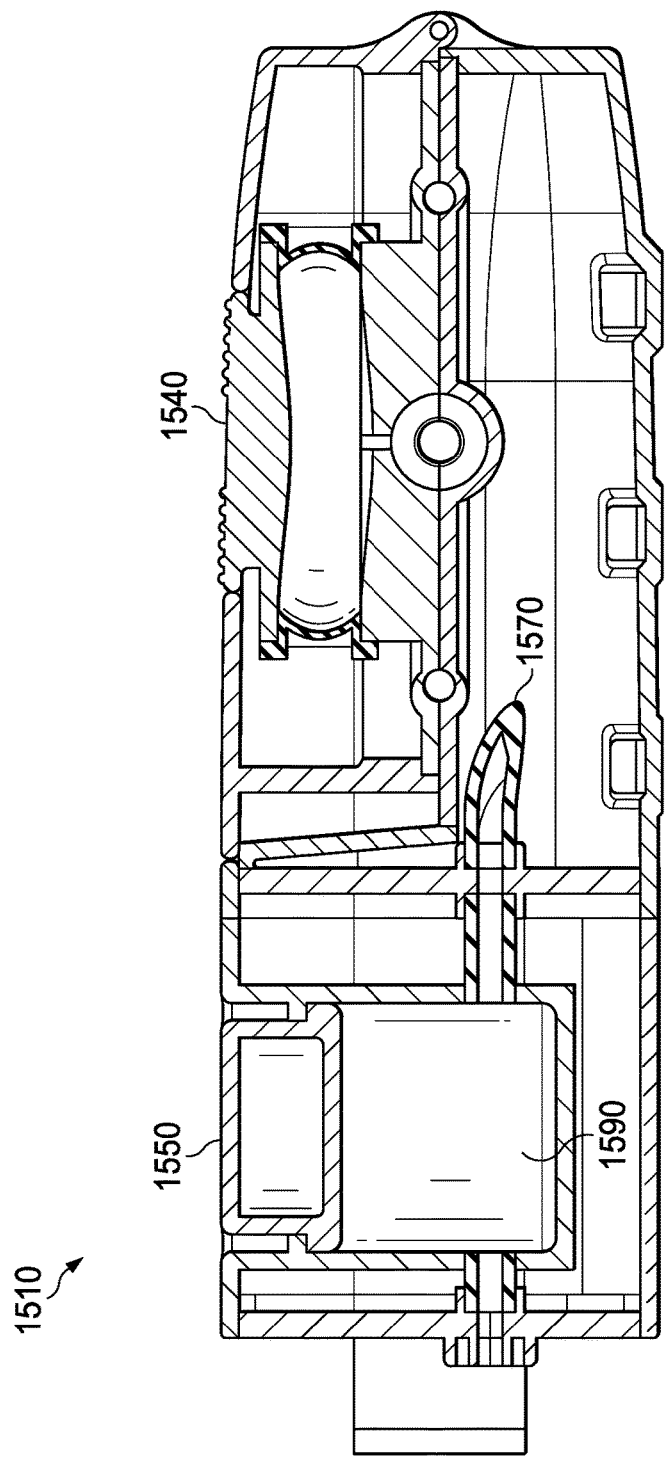
FIG. 15 illustrates a cross-section of an embodiment of the staging or "dual action" specimen delivery apparatus.

FIG. 15 illustrates a cross-section of one embodiment of the staging or dual action specimen delivery apparatus 1510. The first actuator 1540 (such as the previously described first bulb) propels a fluid through the fluid transport path. The propulsion may strip sample from clinical tool (e.g., swab or other suitable sample collection device) and otherwise mixes the fluid with the sample. The fluid and sample mixture are transported to the staging chamber 1590 via the fluid transport path which may include channels or fluid transport tubes such as rifled fluid transport tube 1570. When the specimen is ready to be delivered to the next stage of the medical diagnostic system, the user can depress the second actuator 1550. In the illustrated embodiment, the second actuator and staging chamber operate in a manner similar to a syringe to drive the prepared specimen from the staging chamber to the next stage of the medical diagnostic system.

In one embodiment, the next stage of the medical diagnostic system signals when it is ready to accept the specimen (i.e., when the user is cleared to depress the second actuator). In other embodiments, the next stage actively communicates with the specimen delivery apparatus through one or more ports on the backplane to either aid in the preparation of the specimen or to determine or signal when the specimen has been adequately prepared and is ready to be delivered to the next stage of the point-of-care medical diagnostic system.

For example, the staging chamber may be positioned adjacent a transducer for applying at least one of a thermal, mechanical, acoustical, or optical energy to the contents of the staging chamber. A thermal pad, for example, may be used to heat the contents of the staging chamber to a pre-determined temperature. Thermal, mechanical, or acoustical energy may be used for lysis.

The staging chamber may also be equipped with sensors to permit detection of threshold conditions that determine whether the specimen has been prepared appropriately. The sensors also enable controlled application of thermal, mechanical, acoustical, or optical energy to the contents of the staging chamber with the control provided by the next stage of the point-of-care medical diagnostic system. An optical sensor may be used to determine if certain chemical reactions are complete, for example. A thermal sensor may be used to monitor the temperature of the contents of the staging chamber. Power, sensor, and control signals may be communicated between the next stage and the specimen delivery apparatus through electrical ports on the backplane of the specimen delivery apparatus.

Figure 16:
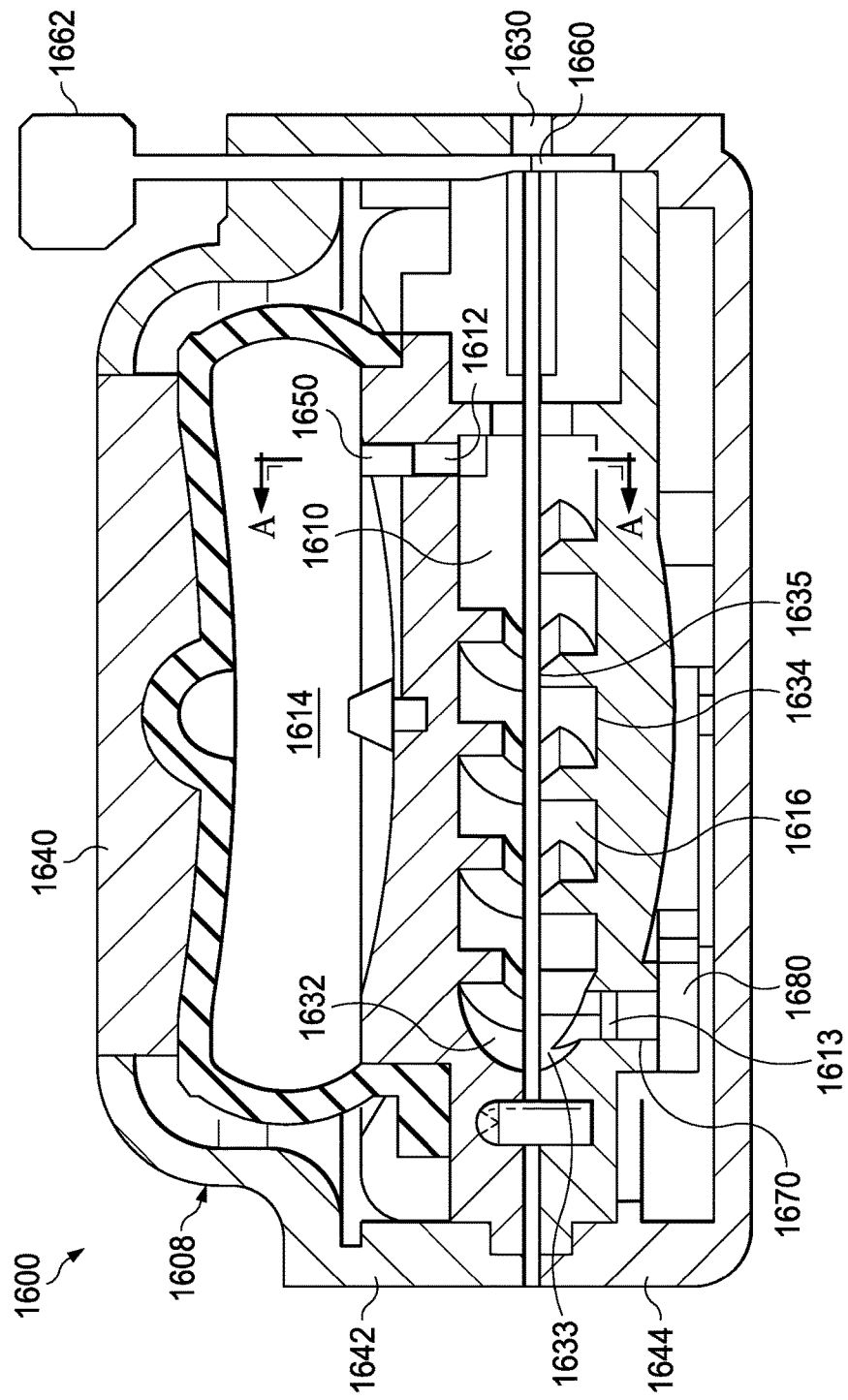
FIG. 16 illustrates a cross-section view of an embodiment of a specimen delivery apparatus.

FIG. 16 shows an embodiment of a specimen delivery apparatus 1600 that is analogous to the embodiments described above (see, e.g., FIG. 7A). The specimen delivery apparatus 1600 includes a housing 1608 that in turn includes first housing portion 1642 and a second housing portion 1644 coupled together at a hinge (not shown) such that the first housing portion 1642 and second housing portion 1644 are operable to move relative to one another to transition from an open state to a closed state. The housing 1608 includes a collection device receiving area 1630 formed by voids in the adjoining first housing portion 1642 and second housing portion 1644. To that end, the first housing portion 1642 includes a first cavity portion 1632 and the second housing portion includes a second cavity portion 1633. The first cavity portion 1632 and second cavity portion 1633 adjoin to form a chamber 1610, which may be a sealed chamber and may be referred to as a roiling chamber. Here, the "roiling chamber" is a chamber used for receiving a swab or other suitable sample collection device and facilitating the flow of liquid over and through the swab or other collection device for the purpose of eluting and recovering a substance of interest (e.g., a specimen) from the swab or other suitable sample collection device. The chamber 1610 may have baffling, grooves, or other similar structures that alter the flow of the fluid over the swab or other suitable sample collection device in such a way as to increase the degree of elution.

The first housing portion 1642 further includes a fluid supply reservoir 1614, which may be a blister pack, as described with regard to the previous embodiments, or any other suitable fluid supply source. The first housing portion 1642 further includes an actuator 1640, which may be a button, a surface of a bulb, plunger, or other similar device that may be depressed or otherwise triggered by a user to positively pressurize or deliver a compressive force to the fluid supply reservoir 1614. When the housing 1608 is in the closed state, the fluid supply reservoir 1614 is fluidly coupled to the chamber 1610 via an inlet port 1612. In some embodiments, the fluid supply reservoir 1614 may be isolated from the chamber 1610 by a destructible seal 1650, which may be the boundary of the fluid supply reservoir 1614 or any other suitable seal. The destructible seal 1650 may be configured to rupture upon being subject to a preselected pressure differential, which may correspond to the actuation of the actuator 1640, to facilitate the flow of liquid from the fluid supply reservoir 1614 to the chamber 1610.

The chamber 1610 is configured to contain a swab or other suitable sample collection device when the housing 1608 is in the closed position. The chamber 1610 includes the inlet port 1612, which receives liquid from the fluid supply reservoir 1614. The chamber 1610 further includes an exit port 1613 coupled to an outlet tube 1670, which may be rifled to facilitate mixing of a liquid as it exits the chamber 1610, as described above with regard to FIG. 7B. In the embodiment of FIG. 16, the exit port 1613 and outlet tube 1670 are positioned in the second housing portion 1644, which further includes a specimen collection reservoir 1680, which may be any downstream area for collecting and/or processing a specimen delivered from the swab or other suitable sample collection device via the exit port 1613 and outlet tube 1670.

Figure 16A:
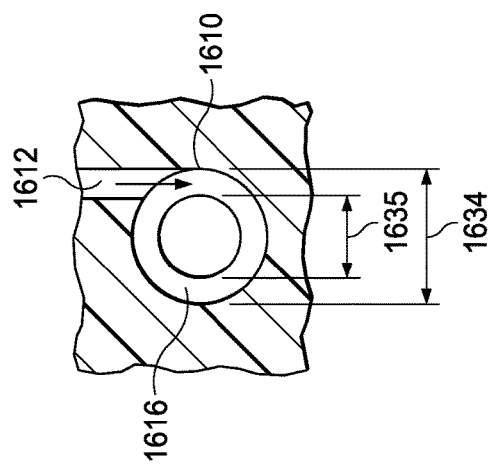
FIG. 16A is a cross-section view, taken along the lines A-A of FIG. 16, showing a portion of a specimen receiving chamber of the specimen delivery apparatus.

The chamber 1610 includes grooves, raised thresholds, or other fluid director features to direct the liquid flowing through the chamber 1610 from the inlet port 1612 to the exit port 1613. In the embodiment of FIG. 16, a groove 1616 is shown that defines a chamber outer diameter 1634 and a chamber inner diameter 1635, corresponding (respectively) to the outer surface and inner surface of the groove 1616. In the embodiment, the groove 1616 forms one or more helical or spiralized channels in the outer surface of the chamber 1610. Here, the first cavity portion 1632 of the chamber 1610 includes inlet port 1612 and grooved or raised features that form a portion of the fluid transport path. Similarly, a second cavity portion 1633 includes exit port 1613 and also includes the groove 1616 (or raised features) that forms a portion of the fluid transport path. To facilitate spiralized flow or a vortexing effect through the chamber 1610, the inlet port 1612 may be aligned with a circumferential flow path through the chamber 1610 that is offset from the longitudinal axis of the chamber 1610 and substantially aligned with a median circumference of the groove 1616, as indicated by the directional arrow shown in FIG. 16A.

As described above, the grooved or raised features of the chamber 1610 increase the shear forces of the liquid flowing through the chamber 1610 and direct the liquid about the surface of the swab or other suitable sample collection device to extract the sample. The roiling effect caused by these features also enhances mixing of liquid injected from the fluid supply reservoir 1614 with the sample. To facilitate maintaining the position of the swab or other suitable sample collection device within the chamber 1610, the housing 1608 includes a cutter 1660 that is actuated by a button 1662 such that depressing the button 1662 results in the cutter 1660 severing the shaft of the swab or other suitable sample collection device while allowing a portion of the swab or other suitable sample collection device that includes the sample collection medium or substrate to remain sealed within the chamber 1610.

Figure 17:
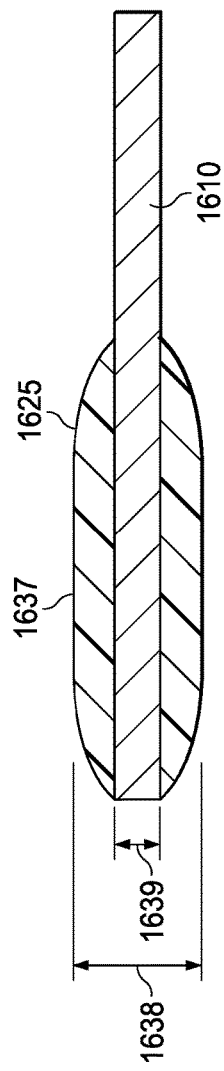
FIG. 17 is a cross-section view of an embodiment of a collection device used to collect a sample.

In view of the foregoing, an exemplary collection device 1625 is described with regard to FIG. 17. The collection device 1625 includes a supporting substrate 1636, which may be a shaft, and a collection substrate 1637. The collection substrate 1637 is operable to absorb or otherwise capture a sample, and surrounds at least a portion of the supporting substrate 1636. To that end, the collection substrate 1637 has a collection device inner diameter 1639 that corresponds to the diameter of the supporting substrate 1636 and a collection device outer diameter 1638 that corresponds to the outer profile of the collection device 1625. The collection device outer diameter 1638 may be constant or may vary depending on the shape of the collection device 1625. For example, the collection device outer diameter 1638 may vary in the case of a collection device 1625 having an oval or tear drop-shaped collection substrate 1637.

Figure 18:
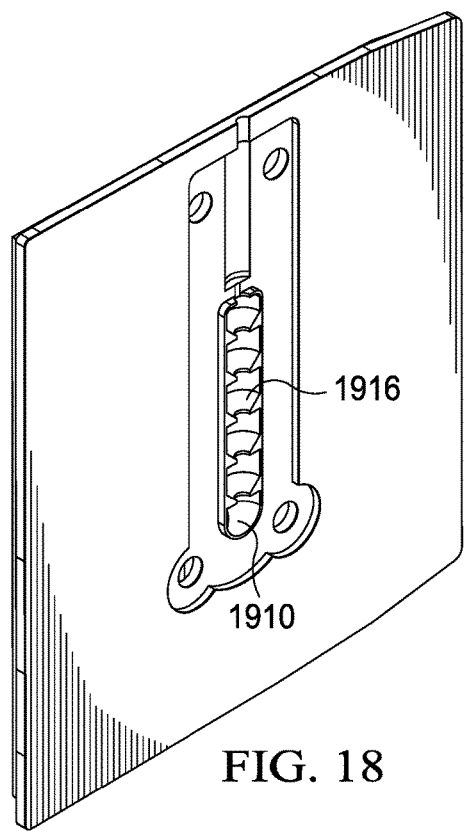
FIG. 18 is a perspective view of one of two complementary halves of an embodiment of a specimen receiving chamber including baffles having a semi-conical profile and a chamfered edge.

FIG. 18 shows a portion of an embodiment of a chamber 1910, wherein the chamber 1910 includes a series of baffles 1916 having a semi-conical profile. Each of the baffles 1916 resembles a funnel wherein the upstream portion (relative to the fluid flow path of the specimen delivery apparatus) of the baffle 1916 has an outer diameter that is equivalent to the diameter of the chamber 1910 and the downstream portion of the baffle 1916 has a chamfered edge defining an inner diameter that is smaller than the outer diameter. In such embodiments, the inner diameter of the baffle 1916 may be only nominally larger than the diameter of a shaft of a collection device (e.g., a swab).

Figure 19:
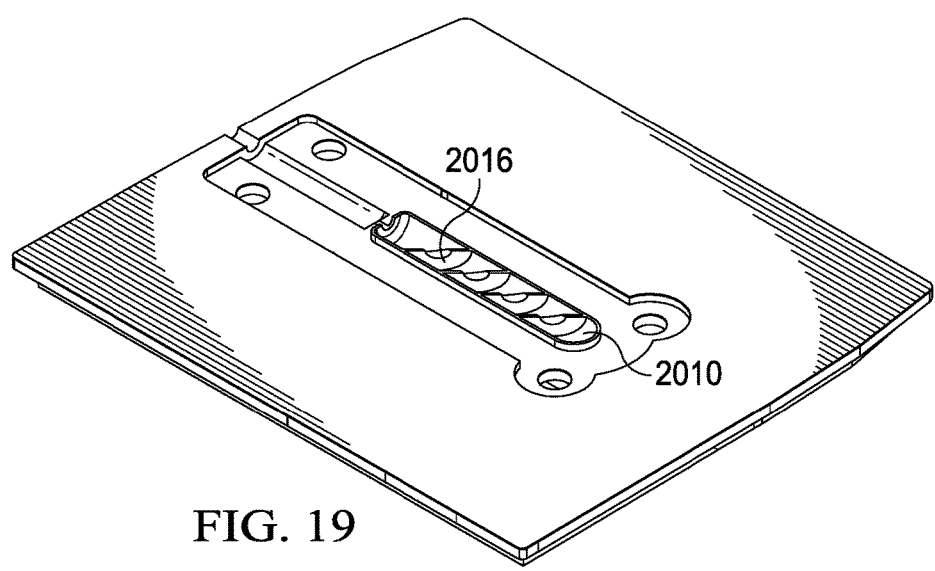
FIG. 19 is a perspective view of one of two complementary halves of an embodiment of a specimen receiving chamber, wherein the chamber includes a fluid guide having a continuous raised edge defining a helical profile along the surface of the chamber.

FIG. 19 shows a portion of an embodiment of a chamber 2010, wherein the chamber 2010 includes a fluid guide 2016 having a continuous raised edge or protrusion defining a corkscrew, or spiral shape through the center portion of the chamber 2010, and a cylindrical cutout at the center that is sized and configured to receive the shaft of a collection device.

In the preceding detailed description, the invention is described with reference to specific exemplary embodiments thereof. A specimen delivery apparatus for in vitro medical diagnostic devices is described. The features of different embodiments disclosed may be combined in order to expand the versatility of the specimen delivery apparatus. Various modifications and changes may be made thereto without departing from the broader scope of the invention as set forth in the claims. The specification and drawings are, accordingly, to be regarded in an illustrative rather than a restrictive sense.

What is claimed is:
1. A specimen processing apparatus comprising:
a housing having a fluid supply reservoir, a specimen receiving chamber, a specimen collection reservoir, and an actuator coupled to the fluid supply reservoir; and
a liquid flow path extending from the fluid supply reservoir to the specimen receiving chamber, and to the specimen collection reservoir,
wherein the actuator is operable to propel a liquid from the fluid supply reservoir to the specimen receiving chamber,
wherein the specimen receiving chamber comprises an inlet port, an outlet port, and a fluid flow guide disposed between the inlet port and the outlet port,
wherein the fluid supply reservoir is fluidly coupled to the inlet port and the outlet port is fluidly coupled to the specimen collection reservoir,
wherein the inlet port is aligned with a circumferential surface of the specimen receiving chamber, and
wherein the specimen receiving chamber comprises a swab shaft seal comprising one or more circular seals operable to engage and form a fluid seal against a shaft of a sample collection device.
2. The specimen processing apparatus of claim 1, further comprising
a destructible seal disposed between the specimen receiving chamber and the fluid supply reservoir, the destructible seal being operable to prevent fluid communication through the inlet port while intact,
wherein the actuator is operable to compress the fluid supply reservoir above a preselected threshold, and wherein the destructible seal is operable to rupture upon being subjected to a pressure differential that corresponds to the preselected threshold, and wherein the actuator is further operable to communicate fluid through inlet port when the destructible seal is not intact.

3. The specimen processing apparatus of claim 1, wherein the housing comprises a first housing portion and a second housing portion, wherein the first housing portion is coupled to the second housing portion at a hinge, wherein the housing is operable to transition from an open state to a closed state when the second portion is rotated about the hinge toward the first portion.

4. The specimen processing apparatus of claim 3, wherein the first housing portion includes a first cavity and the second housing portion includes a second cavity, and wherein the first cavity and second cavity are joined to form the specimen receiving chamber when the housing is in the closed state.

5. The specimen processing apparatus of claim 1, wherein the fluid flow guide comprises a spiralized fluid flow guide.

6. The specimen processing apparatus of claim 1, wherein the fluid flow guide comprises a raised profile having a chamfered edge.

7. The specimen processing apparatus of claim 1, wherein the fluid flow guide comprises a plurality of baffles.

8. The specimen processing apparatus of claim 7, wherein each of the plurality of baffles comprises a chamfered edge.

9. The specimen processing apparatus of claim 1, wherein a planar surface of the inlet port is substantially tangential to a circular, internal surface of the specimen receiving chamber.

10. A specimen processing apparatus comprising:
a housing having a fluid supply reservoir, a specimen receiving chamber, a specimen collection reservoir, and an actuator coupled to the fluid supply reservoir; and
a liquid flow path extending from the fluid supply reservoir to the specimen receiving chamber, and to the specimen collection reservoir,
wherein the actuator is operable to propel a liquid from the fluid supply reservoir to the chamber,
wherein the specimen receiving chamber comprises an inlet port, an outlet port, and a fluid flow guide disposed between the inlet port and the outlet, the fluid flow guide being operable to increase the turbidity of the liquid as it is propelled from the inlet toward the outlet,
wherein the fluid supply reservoir is fluidly coupled to the inlet port and the outlet port is fluidly coupled to the specimen collection reservoir, and
wherein the inlet port is oriented to direct fluid into the specimen receiving chamber in a direction that is perpendicular to and offset from a longitudinal axis extending from a first end of the specimen receiving chamber to a second end of the specimen receiving chamber and coaxial with a generally circular cross-section of the specimen receiving chamber, and
wherein the specimen receiving chamber comprises a swab shaft seal comprising one or more circular seals operable to engage and form a fluid seal against a shaft of a sample collection device.

11. The specimen processing apparatus of claim 10, wherein the inlet port comprises a fluid flow directing surface that is operable to direct fluid into the specimen receiving chamber along a vector that is perpendicular to and offset from the longitudinal axis of the specimen receiving chamber.

12. The specimen processing apparatus of claim 11, wherein the inlet port comprises a first planar surface that is parallel to and offset from the longitudinal axis of the specimen receiving chamber and a second planar surface that is angled relative to the first planar surface such that the second planar surface converges toward the first planar surface where the inlet port joins a cavity of the specimen receiving chamber.

13. A method of preparing a specimen comprising:
collecting a sample using a collection device, the collection device comprising a support substrate and a sample collection material surrounding at least a portion of the support substrate; and
capturing at least a portion of the collection device that includes the sample collection material within a specimen receiving chamber of a specimen processing apparatus, the specimen receiving chamber comprising an inlet port, and an exit port;
wherein the specimen processing apparatus further comprises:
a housing having a fluid supply reservoir, a specimen collection reservoir, and an actuator coupled to the fluid supply reservoir, a fluid flow guide disposed between the inlet port and the outlet port, and a liquid flow path extending from the fluid supply reservoir to the specimen receiving chamber, and to the specimen collection reservoir, wherein the actuator is operable to propel a liquid from the fluid supply reservoir to the specimen receiving chamber, wherein the fluid supply reservoir is fluidly coupled to the inlet port and the outlet port is fluidly coupled to the specimen collection reservoir, and wherein the inlet port is aligned with a circumferential surface of the specimen receiving chamber, wherein the specimen receiving chamber comprises a swab shaft seal comprising one or more circular seals operable to engage and form a fluid seal against a shaft of a sample collection device.

14. The method of claim 13, wherein the specimen receiving chamber comprises a spiral-shaped fluid flow guide arranged on an interior surface of the specimen receiving chamber.

15. The method of claim 13, further comprising actuating a fluid supply reservoir of the specimen processing apparatus.

16. The method of claim 15, further comprising propelling a liquid from the inlet of the specimen receiving chamber to the outlet of the specimen receiving chamber.

17. The method of claim 16, wherein propelling the liquid from the inlet of the specimen receiving chamber to the outlet of the specimen receiving chamber comprises suspending at least a portion of the sample in the liquid.

18. The method of claim 17, wherein propelling the liquid from the inlet of the specimen receiving chamber to the outlet of the specimen receiving chamber comprises propelling the liquid across a fluid flow guide and increasing the turbidity of the liquid as it flows from the inlet toward the outlet.

19. The method of claim 18, wherein the fluid flow guide comprises a raised profile having a chamfered edge.

20. The method of claim 18, wherein the fluid flow guide comprises a plurality of baffles.

* * * * *